United States Patent [19]
Slavin

[11] Patent Number: 4,698,564
[45] Date of Patent: Oct. 6, 1987

[54] SPINNING OPTICS DEVICE

[76] Inventor: Sidney H. Slavin, 9505 Carterwood Rd., Richmond, Va. 23229

[21] Appl. No.: 742,416

[22] Filed: Jun. 7, 1985

Related U.S. Application Data

[62] Division of Ser. No. 151,585, May 20, 1980, Pat. No. 4,522,474.

[51] Int. Cl.[4] ......................... H02P 1/22; G02C 1/00; A61B 3/00

[52] U.S. Cl. .................................. 318/257; 128/76.5; 351/158; 351/203; 351/246

[58] Field of Search .................. 351/41, 158, 203, 84, 351/200, 246; 318/255, 256, 264, 268, 272, 280, 281, 283, 567, 569, 570, 571, 138, 254, 439; 128/76, 5

[56] References Cited

U.S. PATENT DOCUMENTS

| | | | |
|---|---|---|---|
| 2,089,863 | 8/1937 | Updegrave | 351/203 |
| 2,718,227 | 9/1955 | Powell | 351/203 |
| 3,168,894 | 2/1965 | Hollander | 351/203 |
| 3,433,219 | 3/1969 | Genevay | 351/203 |
| 3,484,155 | 12/1969 | Praeger et al. | 351/203 |
| 3,544,203 | 12/1970 | Garcia | 351/203 X |
| 3,687,527 | 8/1972 | Blaine | 351/203 X |
| 3,825,735 | 7/1974 | Bowers et al. | 318/569 X |
| 4,270,074 | 5/1981 | Duckworth et al. | 318/254 |

*Primary Examiner*—William M. Shoop, Jr.
*Assistant Examiner*—Bentsu Ro
*Attorney, Agent, or Firm*—Leonard Bloom

[57] ABSTRACT

A monocular and binocular spinning optics device for use by doctors, researchers, etc., that creates a specific visual phenomenon in front of one or both eyes of the person wearing the device wherein the lenses are constructed by cutting out and affixing stick-on type lens material, such as fresnel prisms, polarizing material, colored filters, cylinder prisms, reflective material, etc., to a plano-plastic disc. A drive motor rotates the rotating lens, which is held in registry with a stationary, non-spinning lens by spectacle frames. The direction and speed of the motor and therefore the rotating lens, along with any pauses or repetitions, are controlled by a digital computer containing the visual training program, and the visual training program, as well as the construction of the lenses, can be devised by the orthoptic practitioner.

12 Claims, 15 Drawing Figures

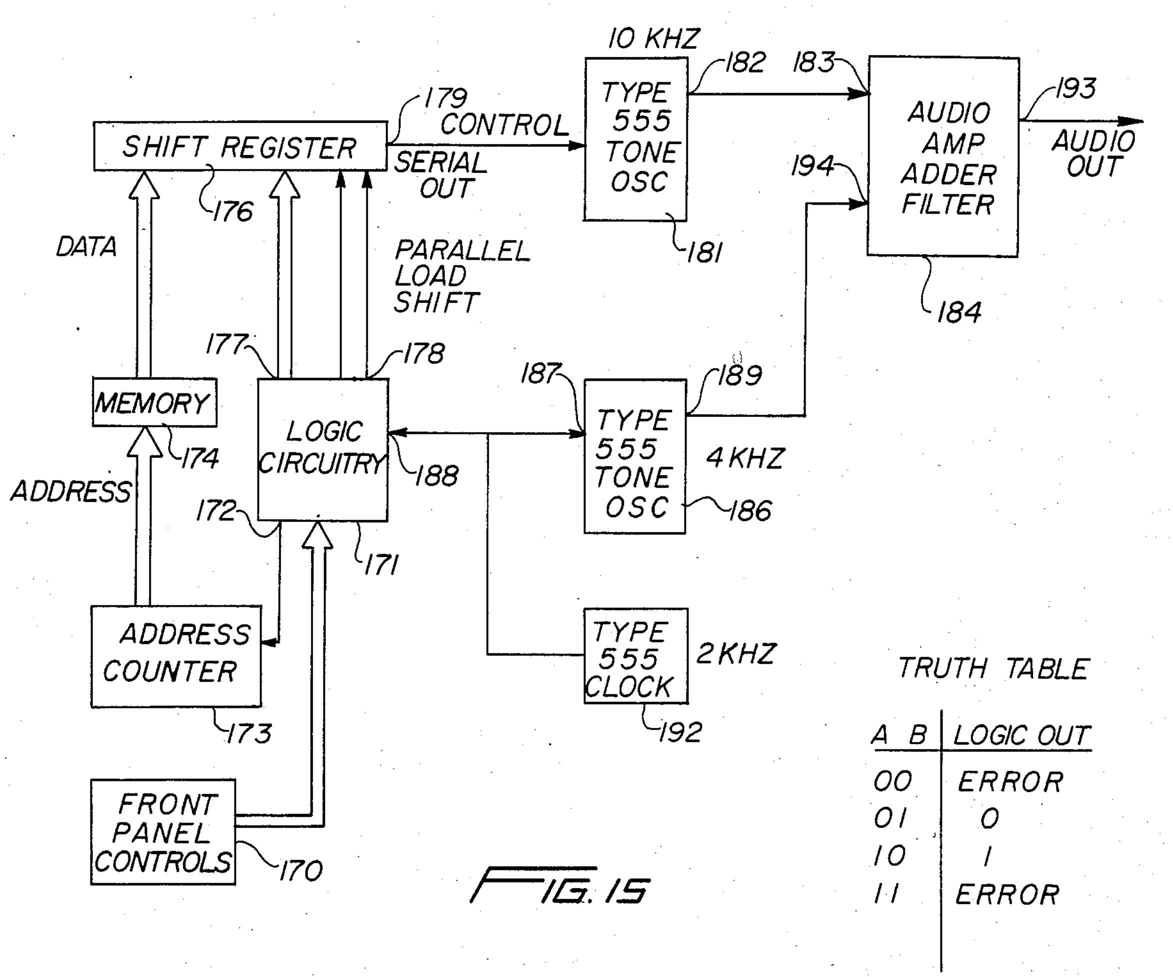
FIG. 15
TRUTH TABLE
| A B | LOGIC OUT |
|---|---|
| 00 | ERROR |
| 01 | 0 |
| 10 | 1 |
| 11 | ERROR |
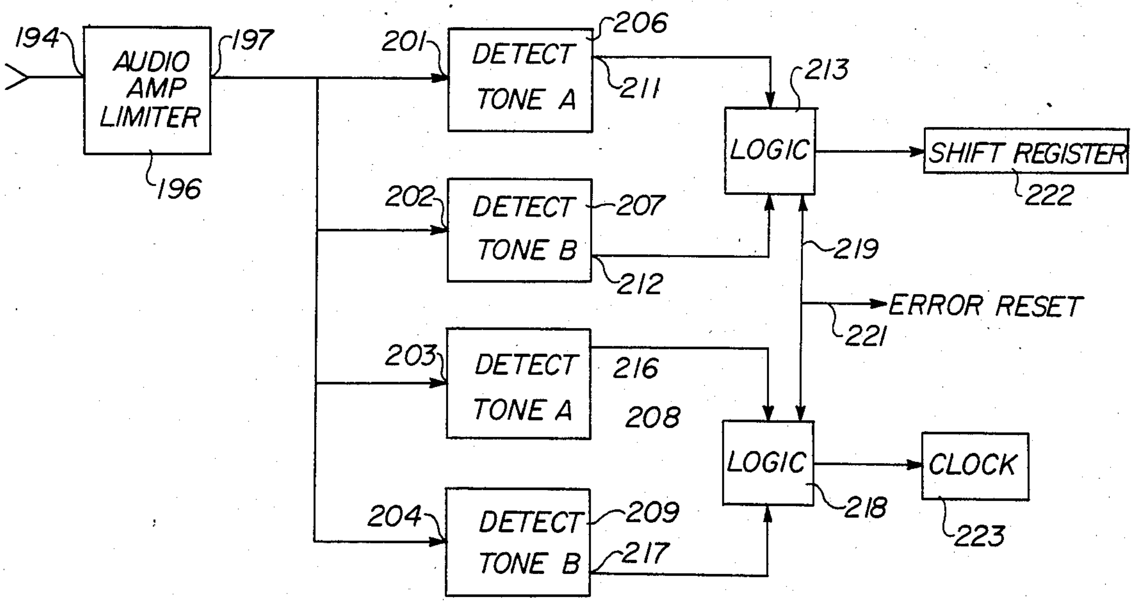

SPINNING OPTICS DEVICE

This application is a division of application Ser. No. 151,585, filed 5/20/80, now U.S. Pat. No. 4,522,474.

BACKGROUND OF THE INVENTION

If visual therapy could be beneficially presented to a patient in his everyday environment (not just in a doctor's office) and still enable the patient to enjoy a reasonably normal life style for eight hours a day during treatment, perhaps one could radically speed up the cure and reduce vision therapy dropouts. This invention will speed up such vision therapy. Out of necessity, to place spinning optics into perspective as a therapeutic tool, some of the present problems in modern orthoptics should be discussed. Three hours a week is probably the maximum vision training exposure for most optometric patients. One week of spinning optics treatment might be equivalent to four and a half months of conventional therapy given the appropriate technology. Fifty-six hours of spinning optics training per week must become possible, assuming training eight hours a day, seven days a week if optometric vision training is to reach the large number of persons that need and can benefit from it.

Spinning optics is of course not new. Daily ophthalmic examination uses spinning optics including a Risley prism where two prisms are aligned at ortho with base-apex of one prism in conjunction with the apex-base of the other. In this system, one prism moves while the other remains relatively constant.

Also commonplace are the rotational effects of contact lenses and the value of prism ballasting for stabilizing toric lenses and bifocal contacts. A number of examples in orthoptics quickly come to mind, though not in the proper chronological sequence. Foremost stands the contribution of Mandaville of Florida, with his Binoculator. The Mandaville apparatus electrically and mechanically rotates prisms and filters monocularly and binocularly. Mandaville mechanically induces variable duction movements of the eyes by step-rotating moving prisms before non-moving prisms. Using a fixed steroscopic lens with rotating prism lenses, it was possible to rotate binocularly fused stereoscopic cards.

The second important innovator was Genevay of New Orleans, who developed a portable rotating Risley prism powered by a small motor with batteries in a flashlight handle. They could be obtained in pairs and one suggested use was for the purposeful induction of diplopia to make it possible for a patient to use his normal suppression mechanism.

Certain entopic phenomenon, both in testing and training, utilize spinning optics. Haidinger brushes uses a rotating polaroid sheet with a blue violet filter. The patient then sees a rotating propeller effect because of Henle's Loop at the fovea. The Rinaldi-Larson Macula Scope is an handheld battery operated version. Maxwell's spot also has been used to distinguish between pathological affectations of the fovea. A purple filter is used and a red spot on a purple background is observed.

M. Allen, of the University of Indiana, has suggested the use of a rotating polaroid and anaglyph material in his Fusionaider. Recently, he has proposed electronically powering a lightweight material resembling a paddle to alternately occlude patient's eyes. The occluder travels within a fixed arc and then reverses direction.

Allen's TBI or Translid Binocular Integrater takes advantage of alpha rhythm and apparent movement along the horizontal axis to break central suppressions.

Kirschner has suggested rotation of movies and cartoons on the wall as a motivating stimulant in vision training. Kirschener also developed a test which requires a patient to wear a miner's headlamp and follow a spinning or rotating target. Use of anaglyphs with appropriate colored rotating lights gives anti-suppression controls.

Critical Flicker Fusion (CFF) though not clinically used often today in optometry has involved spinning filters.

Arneson, with his rotator for visual training used red reflecting lights for a patient to follow in version training.

Also, in psychology, the Archimedes Spiral Rotator has been used in the induction of illusion of reversed rotation and hypnosis. Color wheels have been used for years to determine hue and saturation.

Thus, the literature is replete with many references to spinning instruments, but there is historically little research on driving spheres, cylinders, prisms, and color filters in front of a patient's eyes. This is certainly not surprising, since few researchers have appreciated the value of such spinning. Rather than being a disadvantage, it is herein proposed to utilize the phenomenon advantageously.

The following U.S. Patents appear to be germane to the subject matter of the present invention:

2,718,227 Powell
3,168,894 Hollander
3,484,155 Praeger et al
3,544,203 Garcia.

Hollander teaches the use of a vision trainer in which light bulbs for each eye are pulse varied by timers which are also provided with means to control the light intensity for illuminating targets.

Powell teaches the use of a visual exercising device in which a light bulb array, whose firing sequence may be altered, provides the exercise.

The remaining references show the state of the art further. None of the references cited contemplate a structural or conceptual framework substantially similar to the present invention.

There are at least six instruments used in today's orthoptic routines whose actions can be at least partially substituted by spinning optics instrumentation. They are: the occluder a variable fixator, the rotator, the stereoscope, the cheiroscope and the tachistoscope. The main advantage in adapting spinning optics to their use is training in one's own natural, real space, environment, home and work, not in an unnatural conventional instrument setting of twenty feet or less in the O. D.'s (optometrists) office. Occlusion, fixations and rotations have been an integral part of training for years. A non-instrument steroscope is not a new idea. Any optometrist can make a steroscope lens using base-out and base-in prisms to fuse disparate steroscopic cards. Accommodation and convergence are controlled with appropriate lenspower and prism for viewing distance.

The following classical procedures have been described in great detail by Kehl and other visual training experts. Each can be done in modified form using spinning optics, in either the home or office embodying programs of training.

A. Monocular=versions and rotations, fixations and accomodation. Fixation or versions are movements vertically, horizontally, or obliquely using combinations of such movement. Rotations are circular movements or arcing translatory movements within a 360° circle. Accommodation is any activity using the muscles of accommodation for stimulation, or inhibition or the focusing apparatus.

B. Unfused dissociated=versions, rotations, fixations, and accommodation.

C. Alternating=versions, rotations, fixations and accommodative skill training.

D. Brief overlapping momentary bi-ocular=versions, rotations, fixations and accommodative rock.

E. Binocular=versions, rotations, fixations, and accommodative rock.

F. Rotation with stereoscopic fusion can be performed with spinning optics. A patient can fuse AN and Bu stereoscopic cards or BO (base out) and BI (base in) reading paragraphs while adding a rotational or spinning component to his training. Control marks and plus and minus lenses can be used to compensate for the optical distance when accommodation occurs. Use of anaglyph or polaroid utilizing crossed and uncrossed diplopia created the necessary disparity.

G. Cheiroscopic training can be accomplished during a stage where overlapping and dissimilar images are attempted to be fused. Here the patient attempts to trace in the air, with the finger, the superimposed target from a sideways projected image. A drive motor stops and starts for an appropriate time so the patient's drawing can be completed. A spinning mirror also can be used to move the projected target anywhere within 360° for tracing.

H. Tachistoscopic effects from spinning optics have already been mentioned. Using various materials like variable apertures, and simultaneously combining spinning and non-spinning polaroid filters have enabled us to alter our exposure times to certain moving stimuli.

I. Fixations and rotations using yoked prisms—Obviously, rotational or translatory effect are quite easy to achieve when an instrument can rotate 360°. Yoked prisms are used under two-eyed conditions not to create diplopia but to simultaneously and equally displace the image. Displacement occurs when light has parallel, corresponding locations on the retina. Diplopia occurs with non-parallel, non-corresponding retinal locations. Yoked prisms are a method of creating light displacement but no diplopia when prisms are split between two eyes whose base apex lines are coincident, but whose bases are parallel and both point in a common visual direction to each other. There are two types of yoked prisms which can be made with fresnel optics:

1. Regular yoked prisms are constructed by placing the prism base line 90° to the only Base-Apex line. The triangles' hypotenuse connects between the Apex Base line and the Apex itself.
2. Oblique yoked prisms are constructed by placing the two Base-Apex lines 90° apart and whose base is described by an arc between these two equal Base-Apex lines paralleling the hypotenuse of a theoretical triangle.

J. Electronic Ductions—attempts with a spinning optics device to create simultaneous extended two-eyed movement of the patient's eyes from their original position without creating diplopia. After reaching a certain stopping point, whether diplopia is created or not, electronically ocular movement can be restored back to its earlier binocular single vision state.

To execute a base-in duction, place base-out prism (for example, eight prism diopters) on the right eye and to a similar extent, also base-out on the left. By electronically rotating the right lens clockwise and stopping the rotational movement at each of four quadrants through 360° one will have spun out the right prism from base-out to base-up to base-in to base-down. Simultaneously pairing the identical left lens and spinning it counterclockwise will also move it from a base-out to base-up to base-in to base-down cycle. One can stop the spinning optics device at each quadrant.

To execute a base-out duction, place two identical base-in prisms, one before each eye. The right can rotate this lens counter-clockwise creating in sequence base-in to base-up to base-out to base-down prism. The left eye simultaneously rotates in the opposite direction with a clockwise movement, moving in sequence that lens from base-in to base-uo to base-out to base-down directions.

This is in contrast to yoking prisms which may have equal but complementary horizontal bases (base-out-right eye and base-in-left eye) each simultaneously moving clockwise or counterclockwise in synchronization. By yoking vertical prisms, one starts both right and left eye with prisms in the base-up or base-down position and rotates them synchronously. Yoking movement is only to binocularly displace movement from a preset position.

SUMMARY & OBJECTS OF THE INVENTION

Accordingly, it is a primary object of the present invention to provide a new and novel spinning optics device as a bioengineering tool which is arranged to position the necessary lenses and filters, to spin such lenses and filters in a desired direction for a certain period of time at a particular speed.

Another object of this invention is to provide a new and novel delivery method for optometric-orthoptic services combining training in the patient's ecological environment (home, school office and recreation) with an associated control system.

A further object of this invention is to provide a unique new class of lens designs never before conceived as possible or considered as useful along with a device to spin or drive these special lenses before a patient's eyes.

Still another object of this invention is to provide a new and novel electronic drive system for spinning optics which activates a rotating lens arrangement in a preprogrammed manner.

A still further object of the invention is to provide a new and novel computer operated rotating lens system for the treatment of defective vision which is easily and readily programmable for each patient.

Further objects and advantages of the invention include the provision of a spinning optics device which may be used for selective control/peripheral retinal stimulation; developing of variable spherical and prism lens powers; new concepts of electronic occlusion; yoked prism rotations; new methods in developmental training of infants having amblyopia and strabismus; expansion of conventional orthoptic techniques for anti-suppression training and physiological rehabilitation; The reduction of anomalous retinal correspondence or projection and eccentric fixation patterns; new techniques in training accommodation and reading; electronic ductions; incorporation of stereopsis with rotational movement; motion disturbance induction and treatment; induction of controlled visual-vestibular changes to determine dosage levels in pharmocological research; stroke rehabilitation, a new low vision prosthesis, and an amusement park thrill enhancer.

With conventionally prescribed lenses in a standard frame all points on a given lens maintain a constant and unchanging orientation to gravity. Customarily, the accepted denotations of space x, y and z is identified on a particular face of a patient.

In contrast, it is an object of spinning optics to create a relative and dynamic variation of light, which by definition does not allow (except only momentarily) a parallel relationship of entering light to the patient's constant gravitational orientation. In other words, even though the patient's x, y and z axes may be constant, entering light through spinning lenses parallels the x and y axes of the patient only once in a given rotation. During other times in the same revolution, any portion of the rotating lenses can parallel the same x and y axes also at least once.

With conventional static positioned optics using cylinders or prisms, the axes of the base-apex line is always permanently relative to gravity. With spinning optics, cylinder axes or prism base-axis line vary from moment to mement relative to gravity.

A primary object of spinning optic lenses, filter and instrumentation is to intervene and develop a radical (fundamental but extreme unconventional) approach to anti-suppression eye control therapy. We may attack the visual problem in one of two ways: (a) radically and actively disturbing the leading eye and forcing the less efficient eye to make new interpretive judgments under binocular, but unexpected conditions; (b) or disturb the habitual suppressed eye by extreme spinning of that eye instead. Stimulus generalization can be prevented by using variable and unpredictable motor rotational speeds, timing and directional movements.

It is still another object of the spinning optics incorporated in this invention to permit many conventional and special orthoptic procedures to be automatically executed under conditions not much more complicated nor cosmetically more disrupting than wearing dental training bite stabilizers. Among many tasks accomplished manually which can be automatically programmed on a repetitive basis by spinning optics are:

(1) Patching can be replaced by electronic occlusion. This occlusion can be partial or complete, central, peripheral sectored, binasal, bitemple, superior, homonymous, inferior, staggered, irregular contoured patterned, regular contoured patterns, opaque, translucent and transparent with combinations and variations in materials, colors etc.

(2) Yoked prisms rather than being semi-permanently mounted in a base right position in training spectacles can be changed by the doctor at the flick of a switch to base-right, base-left, base-up, base-down, or any other in between oblique position.

(3) To make a patient aware of diplopia, monocular or binocular, or make a patient aware of visual discrimination change, prisms or filters need to be rapidly changed so comparisons can occur. Electronic spinning of a prism, sphere and filter, when combined under spinning and non-spinning lenses have a disproportionately increased probability of disrupting habitual patterns. This is simply because at instant command are almost infinite options of speed, lens location, directional spin, time of stimulation, aperture opening, etc.

(4) Since motivation is always an important consideration, what child would not want to wear a spaceman's helmet containing the spinning optics hardware? Or Mickey Mouse fun goggles? There is nothing sacrosant in expecting that spinning optics devices for pre-schoolers to look like glasses at all.

Other objects and advantages will become apparent in the following specification when considered in light of the attached drawings herein:

BRIEF DESCRIPTION OF THE DRAWINGS

FIG. 15 is a block diagram for the power supply for the program reader which feeds and codes an office computer program onto the microchip memory in the control circuit.

DESCRIPTION OF THE PREFERRED EMBODIMENTS

The first portion of the following description will focus on the mechanics of the rotary lens system and the lenses used therein. The second portion of the description will concentrate on the electrical and computer components that drive and program the rotating lenses.

Figure 1:
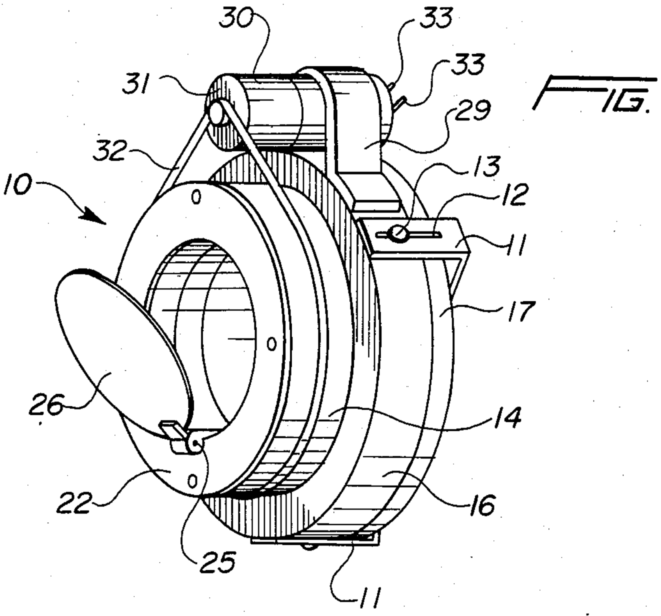
FIG. 1 is a perspective view of a monocular spinning optics device constructed in accordance with the invention.

Referring now to the drawings in detail, wherein like reference characters indicate like parts throughout the several figures, the reference numeral 10 in FIG. 1 refers generally to the monocular spinning optical device of the invention. The device 10 is mounted on spectacle frames (not shown) using a plurality of L-shaped mounting clips 11, which are provided with an adjustment slot 12 for accommodating a mounting screw 13 to enable the device 10 to be mounted on spectacle frames of various sizes.

Figure 2:
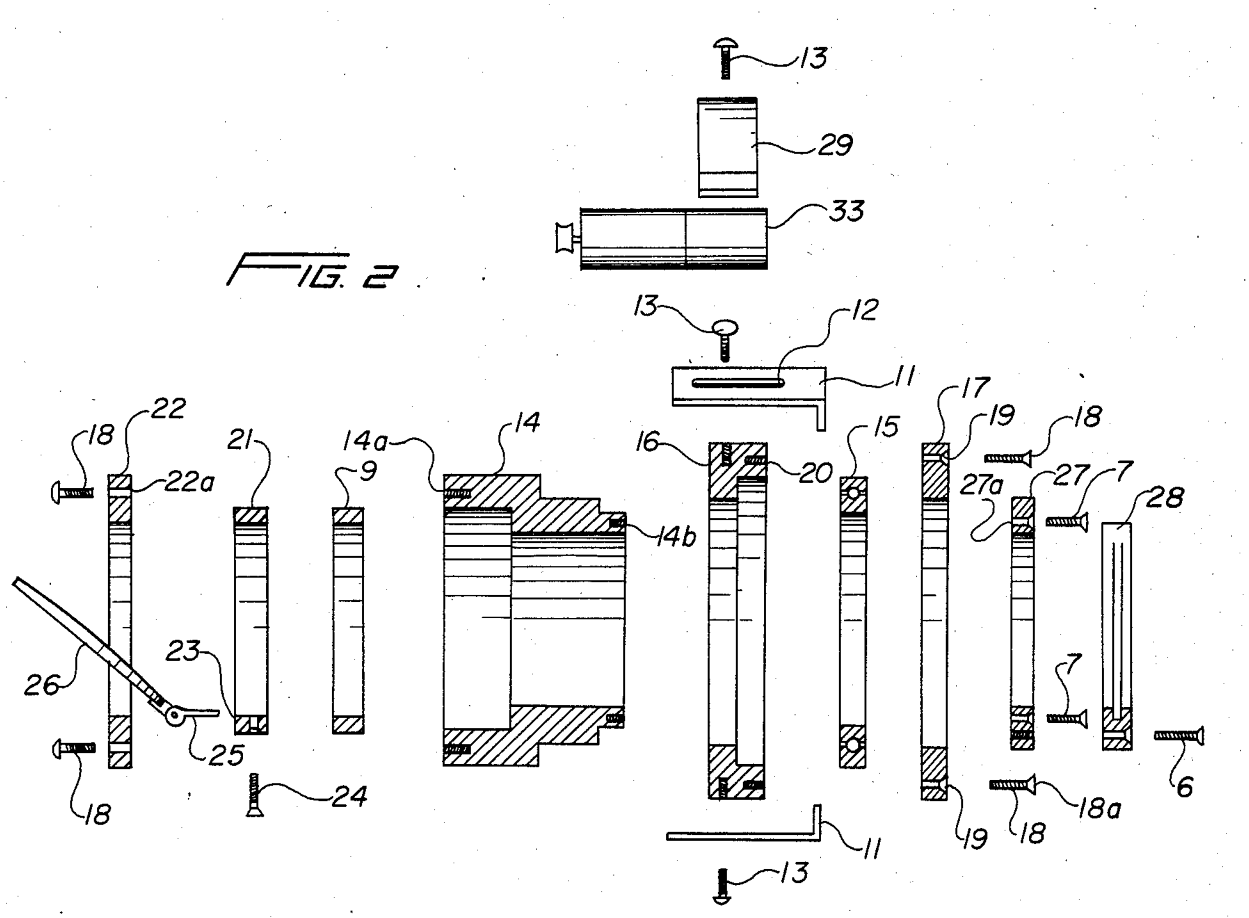
FIG. 2 is an exploded view of the spinning optical device of FIG. 1.

As shown best in FIG. 2, the device 10 includes a trial lens holder 14 which is the primary rotating member and all other elements that are to be rotated are mounted on the holder 14. The trial lens holder 14 is rotatably supported within a ball bearing 15 which is contained within a bearing mount case 16. The bearing 15 is retained in place by a bearing retainer ring 17 which is mounted on the bearing mount case 16 by a plurality of machine screws 18 which are accommodated within apertures 19 in the retainer ring 17 for threaded engagement with threaded recesses 20 provided in the bearing mount case 16.

The machine screws 18 are provided with flat heads 18*a* so that the heads 18*a* are flush with the surface of the retainer ring 17 in the mounted position.

The rotating trial lens holder 14 is arranged to accommodate a rear trial lens mount 9 and a front trial lens mount 21, which are retained in place by a trial lens retainer 22, the trial lens retainer 22 is mounted on the front of the lens holder 14 with machine screws 18 which are accommodated within apertures 22*a* in the retainer 22 for threaded engagement within recesses 14*a* in the lens holder 14.

The front trial lens mount 21 is further provided with an opening 23 for accommodating a set screw 24 for attaching a support bracket 25 of a pivoting mirror 26 to the lens mount 21. The support bracket 25 permits adjustment of the mirror 26 which is preferably of a plano or a convex configuration which may or may not be deployed depending upon the type of treatment being pursued. Also mounted on the rotating trial lens holder 14 is a rotating member retainer 27 which positively locates the lens holder 14 inside the bearing 15. Screws 7 are provided which are accommodated within apertures 27*a* in the retainer 27 for threaded engagement within recesses 14*b* in the lens holder 14.

If a filter is to be employed, a filter is mounted within the filter holder 28, which is attached to the rotating member retainer 27 by a machine screw 6. Essential to this design of spinning optics is the possibility of spinning one lens while simultaneously a second lens is held in a fixed non-rotating posture both of whose optical axes may be congruently aligned.

The devices 10 include a motor, gear train and velocity light encoder assembly 30 mounted on top of the bearing mount case 16 by means of a mounting bracket 29 and a machine screw 13. The motor 30 is mounted so that a pulley 31 on the motor shaft is directly above the rotating trial lens holder 14. The motor pulley 31 is fitted with an elastic belt 32 which runs around the outer perimeter of the rotating lens holder 14. Thus, rotation of the motor pulley 31 for a certain interval will rotate the lens holder 14 a corresponding number of degrees. At the rear end of the drive motor 30 there is provided two electrical contacts 33 arranged to connect to a new and novel control circuit, as will be described hereinafter, for supplying power to the motion in a selected manner.

Figure 3:
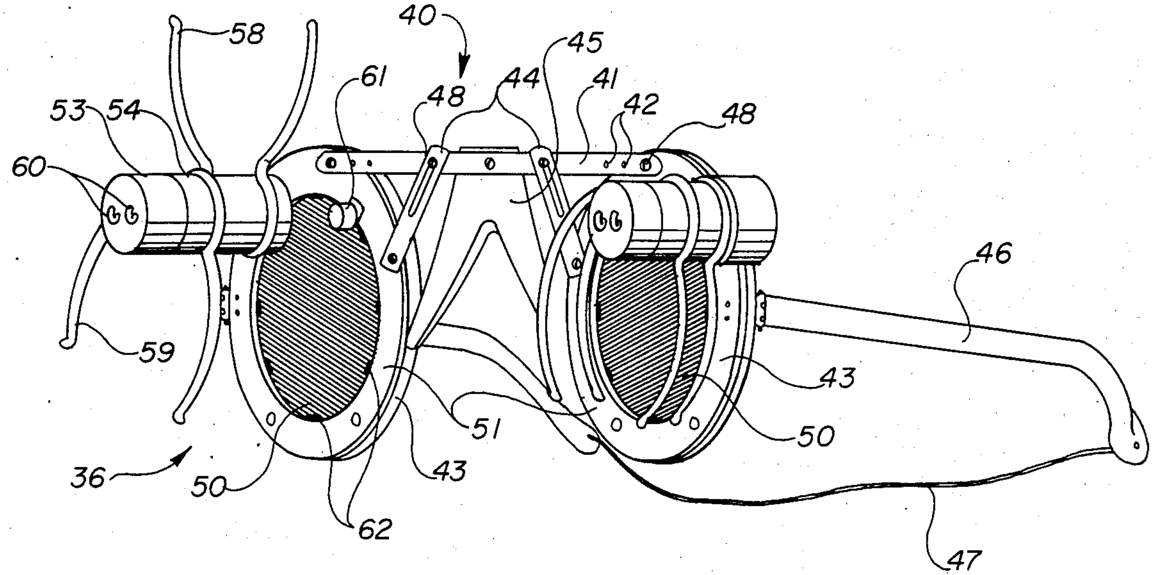
FIG. 3 is a perspective view of a binocular spinning optics device constructed in accordance with the invention.
Figure 4:
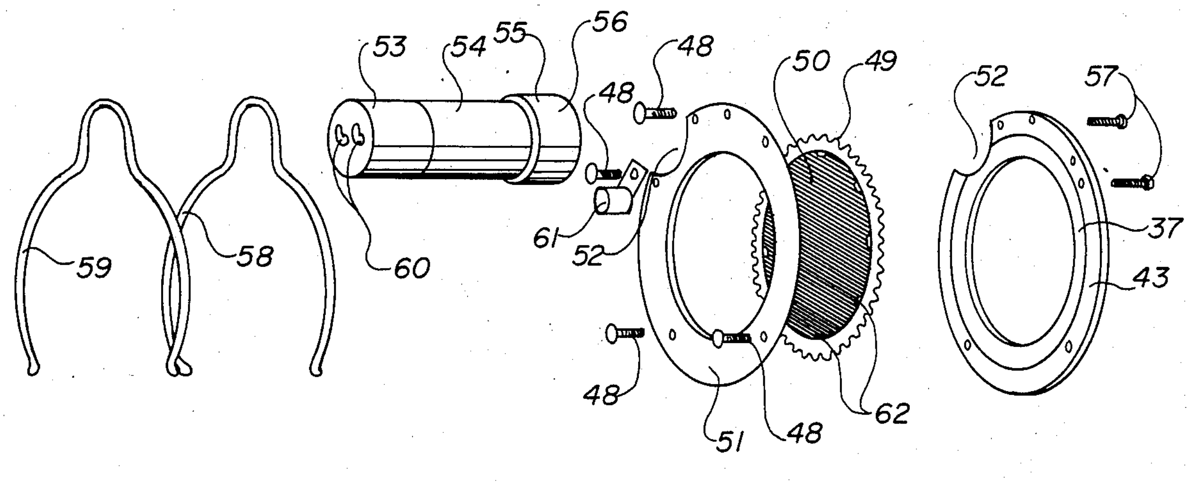
FIG. 4 is an exploded view of a portion of the spinning optics device of FIG. 3.

FIGS. 3 and 4 depict another embodiment of the present invention generally referred to as the binocular spinning optics device and designated generally by the reference numeral 36. In this embodiment of the present invention, spinning optic techniques can be applied to both eyes simultaneously. Instead of a separate pair of glasses two individual units FIG. 4 electronically synchronized can both simultaneously be clipped unto a patient's regular spectacles.

In FIG. 3, reference numeral 40 refers generally to a spectacle frame, the components of which adjust so that the device 36 can be fitted to any individual's head. As shown best in FIG. 3, a stainless steel mounting bar 41 is provided having a plurality of pupil distance mounting adjustment holes 42 which establish the distance between basic mounting rings 43. Slotted, angular swing and stabilizing links 44 are also provided which positively locate the basic mounting rings 43. A Y-shaped nose bridge 45 is affixed to the mounting bar 41 and helps support the spectacle frames 40 on the patient's head. A J-shaped temple piece 46 is pivotally mounted to the outside of each base mounting ring 43 in the conventional manner. In order to prevent the spectacle frames from falling off the patient's head, the ends of the temple pieces 46 are interconnected by an elastic temple cord 47 which fits around the back of the patient's head.

The basic mounting rings 43 are mounted on the spectacle frame 40 with small machine screws 48. An annular recess 37 in each of the basic mounting rings 43 receives a lens 50 which is perimetrically fitted with a plastic gear 49. A gear retaining ring 51 is disposed in overlying relationship with the basic mounting ring 43 to form a circular inner cavity provided by the recess 37 which serves to retain and support the lenses 50 fitted within the annular gear 49 for rotation inside the cavity when driven.

It should be understood that it is within the scope of the invention to use a large varity of lenses 50 according to the requirements of the specific treatment being utilized. More than lenses can spin at the same time. A detailed discussion of the lenses 50 is contained in a latter portion of the present description.

The upper temple quadrant of each basic mounting ring 43 and each gear retaining ring 51 is provided with a arcuate cutaway 52 which exposes the teeth on the plastic gear 49. The drive train assembly of the device 36 includes a drive motor 53, a reduction gear train 54, a spur gear housing 55, and a spur gear 56. One of such drive train assemblies is mounted on each basic mounting ring 43 with a pair of machine screws 57. Each drive train assembly is mounted in such a manner that the spur gear housing 55 is seated within the cutaway 53 with the spur gear 56 in engagement with the plastic lens gear 49. Thus, driving the spur gear 56 rotates the lens 50.

Both the reduction gear train 54 which may have a gear ratio of 330:1 and the drive motor 53 have cylindrical housings which extend in front of the spectacle frame just to the side of each lens 50. A fixed non-spinning rear trial lens retaining clip 58 and a fixed non spinning front trial lens retaining clip 59 are provided which snap onto and rotate about the cylindrical housing of the reduction gear train 54, in such a manner that trial lenses can be held in place directly in front of the rotating lens 50 as shown in FIG. 3. The trial lens retaining clips 58 and 59 also slide laterally on the housing of the reduction gear train 54, so that the distance between the trial lens and the rotating lens 50 can be adjusted. Also, each drive motor 53 is provided with two electrical contacts 60 for connection to the electronic control circuit of the invention as in the embodiment of FIGS. 1 and 2.

Since it is critical to the success of the therapy that the lens 50 rotate exactly as planned, a sensor 61 is provided to detect lens positioning and programming spots 62 are provided on the surface of the rotating lens 50. When a sensor 61 detects a programming spot 62, this means that the lens 50 has rotated a certain number of degrees. This information is used to stop and start the various rotational manuevers contained in the visual training program. A velocity light encoder would be an updated version with self contained LED sensor 61 to track and calculate the program spots.

There are four major rotational strategies for spinning the binocular optics device 36 of the invention. First, both lenses 50 can rotate clockwise. Second, both lenses 50 can rotate counter-clockwise. Third, both lenses 50 can rotate nasally which means that an arbitrary base point selected at the top of each lens 50 moves toward the nose when both lenses rotate nasally. Fourth, both lenses 50 can rotate tempally ie., toward the ears and temple bones. These rotational maneuvers are accomplished by driving the drive motors 53 in either a clockwise or counter-clockwise direction.

Having thus described the mechanical apparatus designed to position and rotate various combinations of lenses, prisms, filters, and mirrors used to create the myriad of visual effects employed in spinning optics to diagnose and treat visual impairment problems, it should be understood that spinning optics often require that the rotating lens be capable of performing multiple functions. For example, one quadrant of the lens may be a polarized filter while another quadrant may need to be a yoked prism or a colored filter. Obviously, the combinations and permutations of lenses, filters, prisms, and mirrors is multitudinous. Therefore, it is necessary to devise a method for the practitioner to construct the various combination lenses required for spinning optics therapy.

Figure 5:
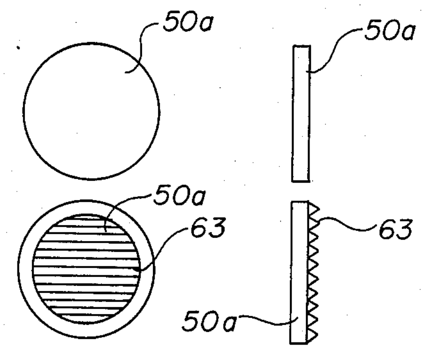
FIG. 5 is a partial representation of a method of forming lens incorporated in the invention.

FIG. 5 illustrates the method of constructing a lens from a thin, transparent, optically clear plastic disc 50*a*. Fresnel lens material is present available in thin, large sheets. Therefore, stick-on lenses can be cut with scissors or the like from a large fresnel sheet and applied to the plastic disc 50*a* with glue, tape, or can be attached via capillary attraction. In FIG. 5, fresnel material 63 is attached to the plastic disc 50*a*. Similarly, filter material, reflective material, spheres, cylinder, prisms and so forth can be cut or mechanically punched out from sheets and applied in the same manner as the fresnel material. It should be noted that both the rotating lenses and the stationary trial lenses can be constructed by the stick-on method.

Furthermore, a lens can be divided into pie-shaped quadrants, or into any other geometric configuration and various materials can be applied to different sectors. The rotating lenses can be used alone, or in conjunction with one or two fixed trial lenses which are held in registry with the rotating lens by the trial lens clips 58 and 59, as shown in FIG. 3. Thus, as the rotating lens rotates and various sectors on the rotating lens register with different sectors on the fixed non spinning trial lens, a myriad of visual phenomena can be achieved. Furthermore, visual phenomena can be created, gradually dissipated, and then re-created within a certain time interval, so that a patient can become more familiar with the parameters of the patient's own visual impairments, and thereby increase the effectiveness and efficiency of visual therapy.

The pairing of spinning with non-spinning lenses is a useful method of accomplishing the following: electronic occlusion, selective central/peripheral retinal stimulation, design of variable powered sphere and prism spinning lenses, and variable tachistoscopic-like aperture effects.

Figure 6:
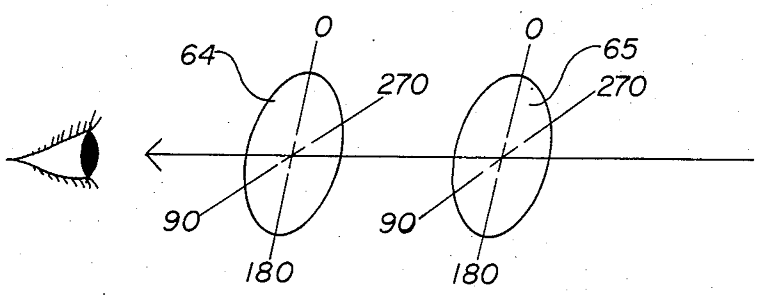
FIG. 6 is an illustration of the relationship between a pair of polarized lens used in electronic occlusion.
Figure 7:
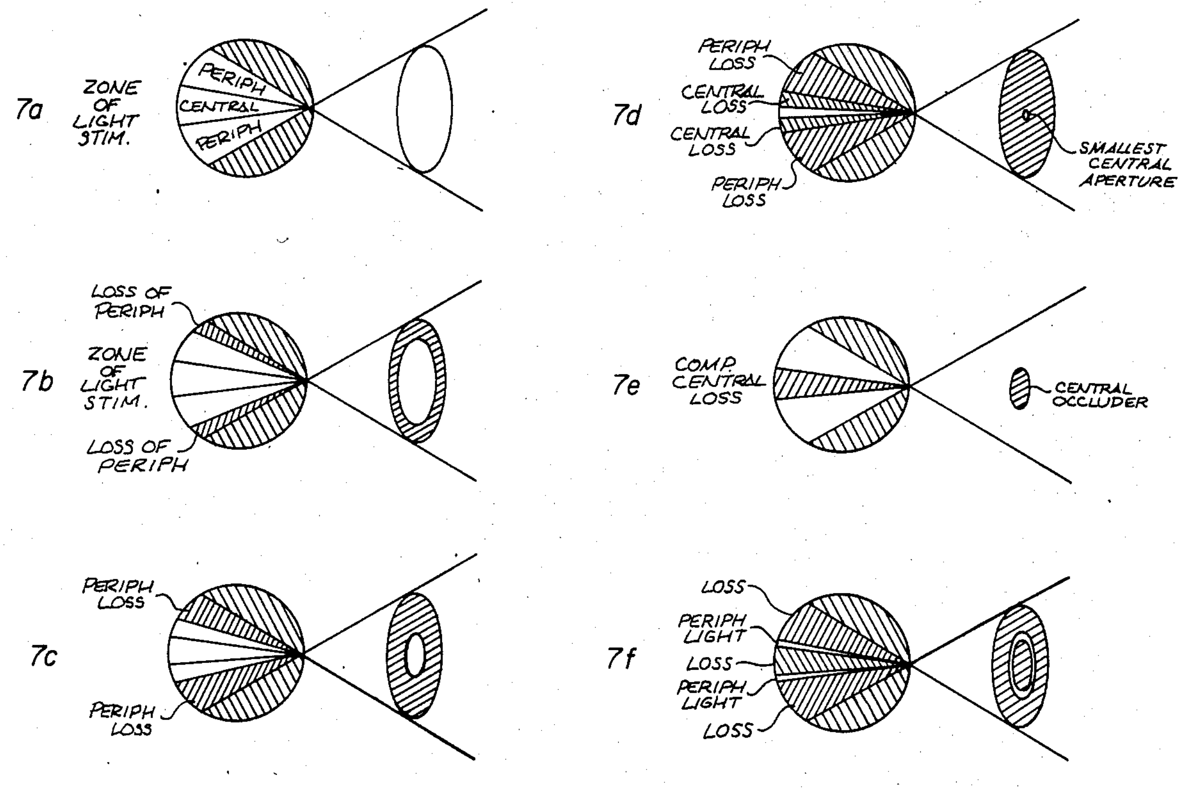
FIG. 7 is a schematic illustration of various combinations of peripheral and central occlusion for the eye performed with the invention.

Electronic occlusion is a technique for rapid and short term eye patching. By spinning a polarized lens filter in conjunction with a non-spinning polarized lens filter, it is possible to fully control light filtration. By way of example and referring now to FIG. 6, a rotating polarized lens 64 and a stationary polarized lens 65 are radially oriented in the same direction so no light filtration occurs. However, as the rotating lens 64 begins to rotate, more and more light is filtered out until filtration, or occlusion, is achieved at 90°. As the lens 64 rotates past 90°, occlusion is gradually attenuated until the 180° position is reached, at which point no filtering occurs, the same as the 0° position. The same cycle is repeated as the lens 64 rotates back to zero position. The same effect can be achieved with red and green or any other pair of complementally colored filters.

Selective central or peripheral stimulation, to amplify or diminish light entering various regions of the eye is achieved by using various polarized sectors on moving and non-moving trial lens discs. To occlude central vision, two polarized discs twelve mm in diameter and exactly centered are positioned, one in the spinning optics rotating device and one in a fixed non-rotating trial lens disc of the device with the axes of polarization 90° apart. As the polarized disc rotates, filtration will vary from maximum occlusion to maximum light transmission. To occlude peripheral vision, both lenses have a central sector of polarized material removed, leaving a plano middle zone. Various combinations of peripheral and central occlusion can be used to vary filtration selectivity, as shown in FIGS. 7A through 7F.

Selective central or peripheral stimulation is an effective method of training attention descrimination. With peripheral occlusion "tunnel vision" is created to emphasize the central figure. Central occlusion creates an emphasis on the background since the central figure is occluded. Thus, those visual impairments formerly treated by patching, can now be treated by electronic occlusion because this form of occlusion can be partial or complete, central or peripheral, or sectored in any selected zone.

Figure 8:
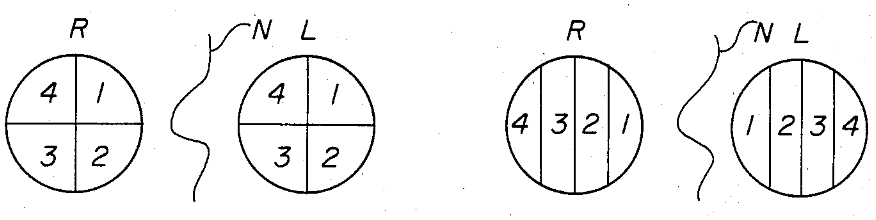
FIG. 8 is a schematic illustration of various lenses divided into quadrants or sectors.

Variable powered prisms and spheres can be created in two ways. One way is to literally cut a number of strips, sectors, zones, etc. of various powers and sizes and attach them together like pieces of a puzzle on top of a plano disc, which may or may not spin. The second way is to use several plano discs each containing at least two powers. One lens will be spinning or moving, the other will be non-moving. In combination, variable power arrangements can be achieved. FIG. 8 shows some general references used to describe lenses that are divided into quandrants or sectors, the two lenses being designated by the letters R (right) and L (left) shown on opposite sides of the patient's nose designated by the letter N. A spinning multi focal can result here.

Figure 9:
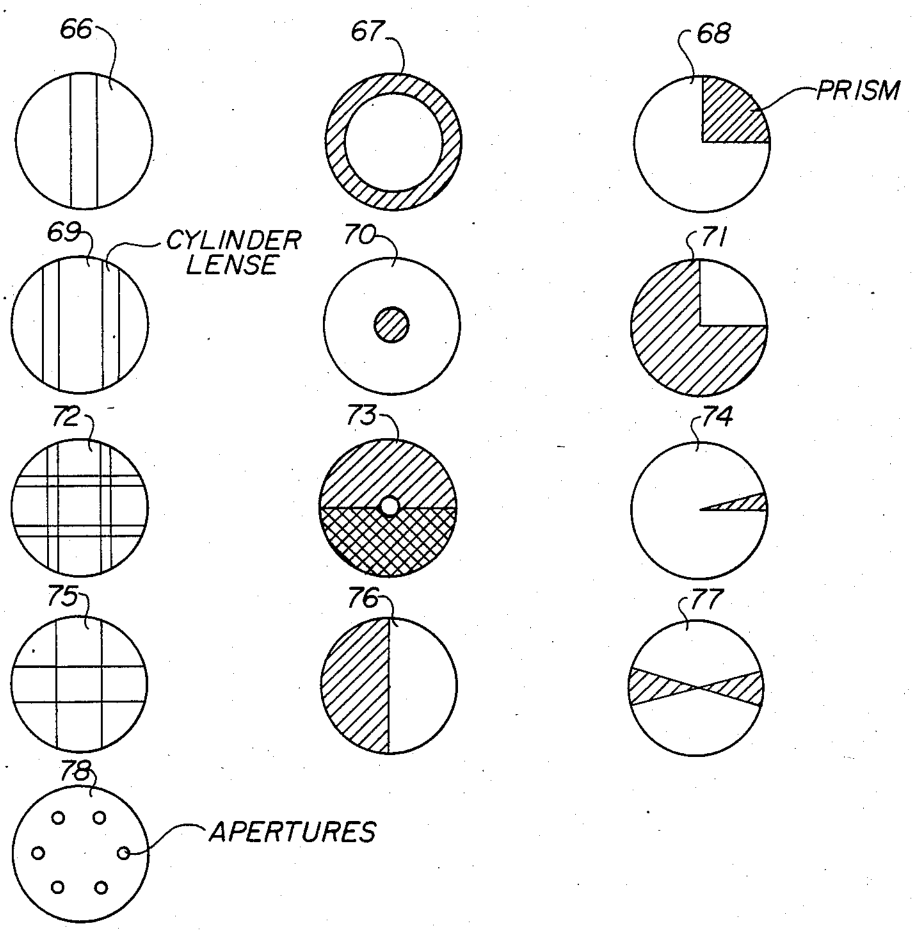
FIG. 9 is a schematic illustration of a variety of lenses for creating a tachistoscopic effects.

Variable tachistoscopic-like aperture effects can be achieved by specifically placing partial occluders throughout a lens. When the occluder is before the line of fixation, nothing can be seen, but as soon as the spinning moves the occluder out of position, the light passing through will be seen. The frequency of light pulsing on and off can be timed. The use of a moving partial occluder 68 with a second non-moving partial occluder 71 creates specific apertures which open and close at specific geographical zones. Reference numeral 78 in FIG. 9 shows one of many possible configurations to create tachistoscopic effects. The other lenses 66 through 77 depicted in FIG. 9 represent a few of the infinite variety of lenses that can be created. FIG. 9 is by no means an exhaustive categorization of the various lens configurations, but is included to display the versatility of the lens construction technique. Furthermore, various filters, occluders, colors, prisms, lenses, and mirrors, etc. can be substituted in any zone to create the desired visual phenomena.

Figure 10:
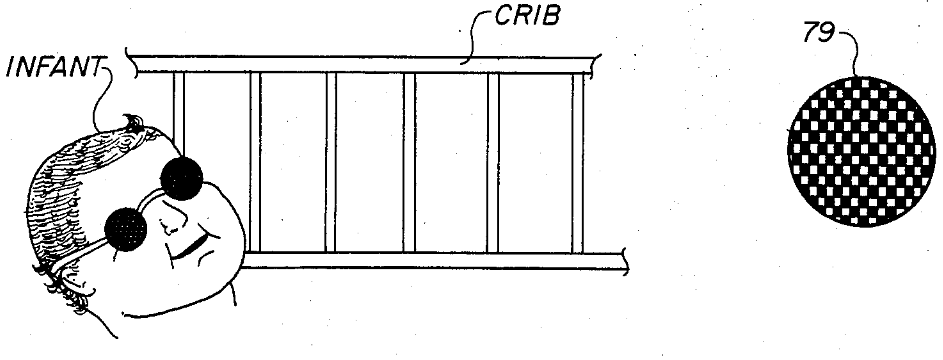
FIG. 10 is an illustration of an infant undergoing treatment using the spinning optics device of the invention.

A detailed description of each embodiment of the present invention would be impractical because the potential uses of a spinning optics device are many indeed. Therefore, the following embodiments have been selected for a brief description to display the versatility of the present invention in the areas of treatment, diagnosis, and experimentation. The areas selected are as follows: (1) infant stimulation programs for youngsters visually damaged at birth; (2) training and practice for ocular motor paresis, and other visual-vestibular orientation problems such as motion disturbance; (3) dynamic visual acuity for driving evaluation and (4) stroke rehabilitation and low vision rehabilitation involving visual field enhancement. These areas are discussed in detail below;

(1) Infant Stimulation Programs for visually damaged youngsters at birth. Already there is overwhelming evidence that the first six months of life are extremely critical for the development of binocular cortical cells in infants. Therefore, when a practioner is confronted with a strabismic infant, the sooner treatment begins, the better. The chances of minimizing early developmental damage to the infant's binocular cortical cells is greatly increased with visual training programs. The training is designed to prevent visual non-correspondence or conflicting correspondence between the two eyes. FIG. 10 shows an infant in his hospital crib. Placed on his face is a goggle-like spinning optics device constructed in accordance with the invention. Repetitive and uniform textured lenses such as the lens 79 in FIG. 10 or striped lenses of set spatial frequencies are spun before the infant's eyes to create a more stimulating effect because of the motion. Since there is a single, uniform field of vision between the infant's eyes, it will facilitate utilization of the infant's binocular cortical cells.

Each infant's bed would be radio-signalled controlled from a central control panel in a nurses' station. Discrete radio signals automatically cut on the device, rotate it clockwise or counter-clockwise, stop, start, pause for a pre-set time interval, and change speed of the spin at will. Furthermore, each child's goggles can have optical sensors to provide a feedback signal whether his eyes are opened or closed and looking in a particular direction of gaze, which will indicate when visual training should commence. All previously mentioned lens designs also can be substituted before either or both eyes.

(2) Training and Practice for Ocular Motor Paresis and other visual vestibular orientation problems such as motion disturbance. The treatment of certain types of motion sickness requires the elimination of conflicting, stressful central-peripheral visual orientation effects and resolution of problems where integration of neuro-pscho-phsiological data is required from either antagonistic or complementary information processing systems. Car motion disturbances have a visual basis and requires improved integration of oculo-motor and accommodative-convergence skill defects through visual training. Moving vertical and/or horizontal yoked prisms may be a useful dis-embedding therapy technique.

Spinning optics can be of value in aviation space flight research, as well as in neuro-physiological studies of nystagmus, diplopia, Meniere's disease, and certain other inner ear disorders.

Spinning the appropriate lenses, usually high powered fresnal prisms, can induce motion disturbance sensations in almost any patient under controlled systematic conditions. This is particularly true when peripheral vision is occluded. Using a 70 rpm rotation speed in a binocular set-up, with one lens moving clockwise and the other counter-clockwise, with a standard twenty diopter prism in each eye, a standardized threshold limit against motion disturbance can be determined for each patient. Thus a preflight screening test for motion disturbance is available. Presently, the Air Force Space Research Centers use complex, expensive rotating rooms which can simulate various "G" forces. In comparison, spinning optics is a very inexpensive method of inducing motion disturbance. It may even have application as a method of making amusement park rides more motion disturbing.

Figure 11:
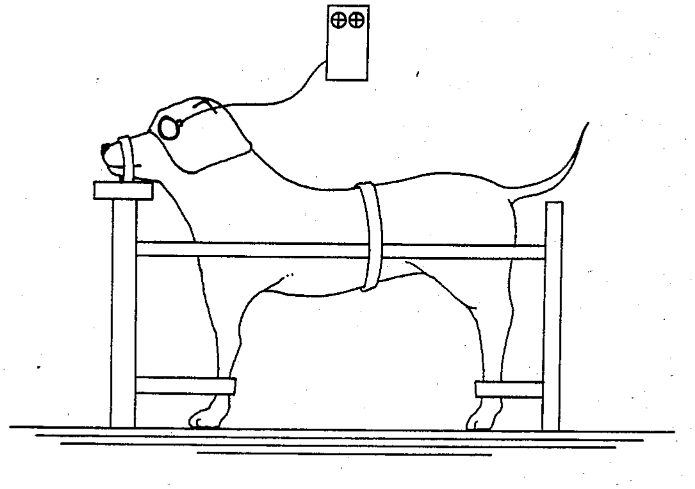
FIG. 11 is a view of a view of an animal on which pharmacological research is conducted using the invention.

To evaluate central nervous system pharmacological effects on the eye using certain anti-cholinergic drugs, such as Dramanine, a systematic program can be designed to induce controlled motion disturbances on a patient and compare threshold effects with and without anti-cholinergic drugs. This type of pharmocological research can also be conducted on animals as depicted in FIG. 11. Here a controlled visual environment may be required using slide projectors.

Oculo-muscles paresis, where oblique muscles, cyclotorsion and/or vertical muscles demonstrate ocular-motor problems has always been a difficult area to treat either surgically or with orthoptics. Spinning optics can be set to specifically rotate muscles: up and out, up and in, down and out, and down and in position or in any other combination of translatory movement pattern.

(3) Dynamic Visual Acuity for Driving Evaluation. Since driving requires the ability to visually gauge different types of motion, a more valuable method of measuring a candidate's visual acumen is to have him recognize images which are themselves moving. This can be achieved by having a candidate wear a monocular or binocular spinning optics device and focus on a Smellen letter chart. The spinning lenses cause the images of the chart to rotate. The speed of the lenses is decreased until the candidate is able to accurately recognize the complete twenty/forty line without error. This would be a measure of his dynamic visual acuity.

(4) Stroke Rehabilitation and Low Vision Rehabilitation involving oculomotor change. Circulatory failure is a common denominator of cerebral-vascular accidents or strokes. Some well known visual pathologies within this population are: hemianopsias, central pinhole vision from retinal destruction, macular hemorrages, central retinal artery and vein occlusions, diplopia, oculo-muscle paresis, loss of mobility, functional loss of eye/hand and eye/foot coordination due to hemiplegias, perceptual confusion both spatially and temporally, and loss of language and speech functions. In the majority of cases, the only orthoptic treatment is temporary occlusion, or patching, where there is intractable diplopia. Few rehabilitation medical centers utilize low vision and binocular vision experts to design hemianopsia mirrors, fresnel prisms, or wide angle inverted telescopes, when there is a severe visual field loss.

Hemianopsia patients, those who lose either the left or right field of vision in both eyes, have many problems. The hemianopsic mirrors in current vogue have limited value, because they are usually permanently fixed in the patient's undamaged seeing field. Unfortunately, the mirror automatically blocks normal fixation when required to shift into that undamaged field. For example, to see into a non-seeing field on the right side, a mirror is placed nasally in front of the right eye in the undamaged visual field. But, if the patient has to look across the left into the undamaged field, there is the additional artificial loss created by the interference of the mirror remaining in the undamaged visual field of that eye. With pinhole vision defects, a patient with a restriction of central vision to 1°–10° limitation, just cannot use a fixed mirror aid. No matter where an extended length mirror is positioned on a spectacle, there are other blind field positions simply because a mirror can only be aimed at one instant only for a particular sector of space where gaze is required. Spinning optics can solve this problem merely allowing 360° of freedom for the mirror to able to be quickly spun into any sector of space. Plano, convex, concave mirrors & prisms in combination or singly can spin in this special aid. They further can be set in any position before the eye at any angle. Normally, this giant mirror will be stored in the superior half of a patient's spectacles out of the way. It is moved as required into the correct position and when no longer needed returned to this superior unobstrusive storage place.

Figure 12:
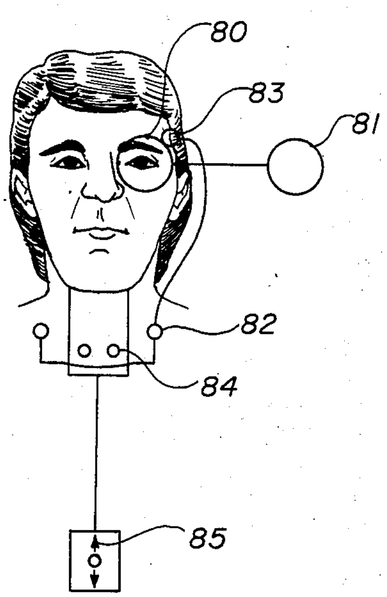
FIG. 12 is a schematic illustration of a patient being treated for hemianopsia or tunnel vision using the spinning optics of the invention.

The spinning optics device shown in FIG. 12 monitors both the angle of gaze of the patient's eye and the rotation of the patient's head. When the patient wants to look to the left the hemianopsic mirror 81 rotates out of the way. In FIG. 12 the spinning optics device is identified by the refererence numeral 80. LED sensors 83 and 82 detect the direction of gaze. Neck detectors 84 detect rotation of the head. Manual over-ride 85 is also provided. When the information from both sensors 82, 83 is coincident, the mirror 81 rotates to a position where it offers the least interference with the patient's undamages visual field or it rotates to a position which offers maximum unimpaired visual field relative to that neck, head eye angulation.

Figures 13, 14:
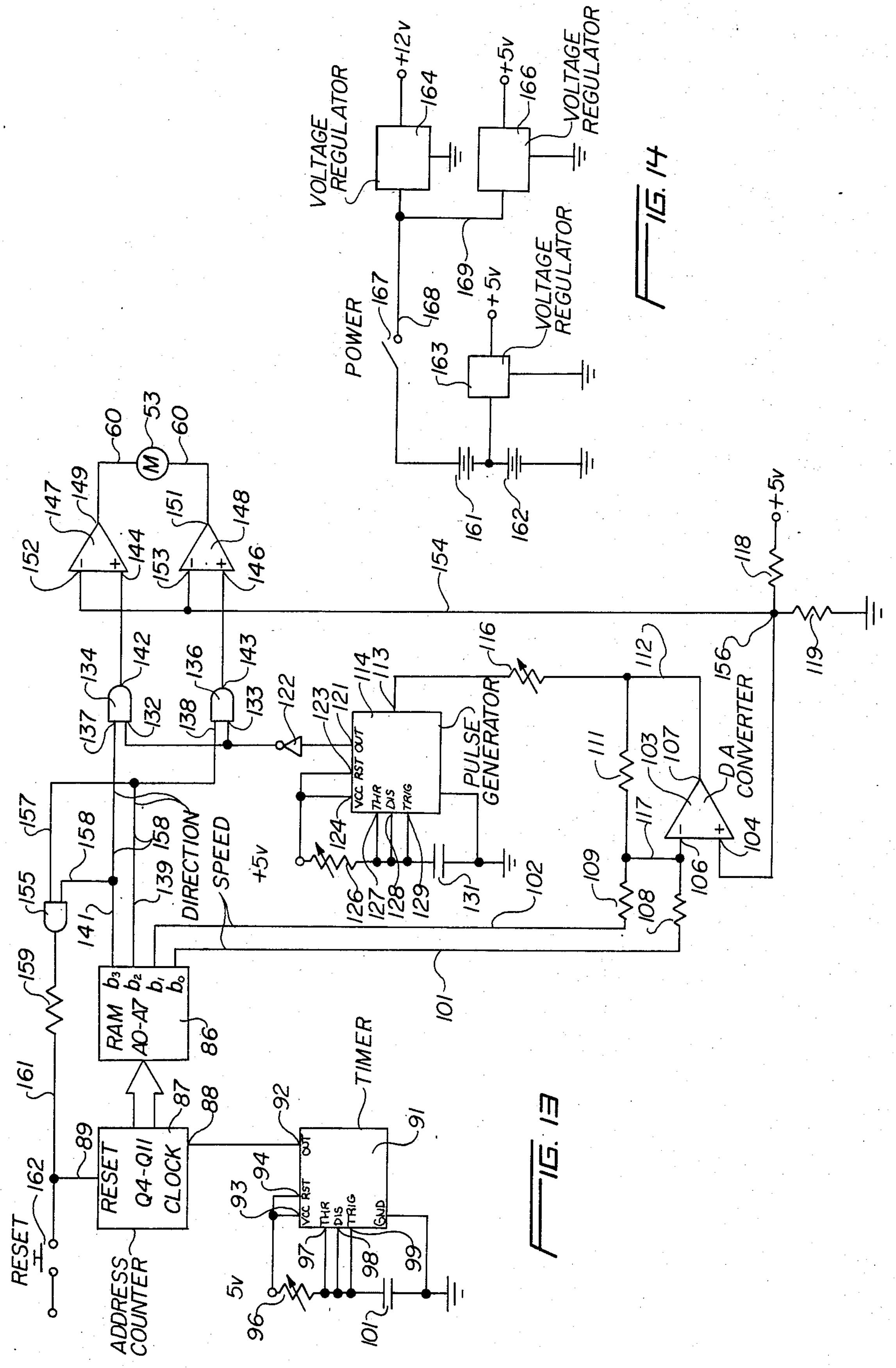
FIG. 13 is a block diagram of the electronic control circuit for the spinning optics device of the invention.
FIG. 14 is a block diagram for the power supply for the control circuit of FIG. 13.

Referring now to the drawings and to FIG. 13 in particular, there is shown an electronic control system for rotating at least one ophthalmic lens which is rotatably mounted on a spectacle frame in the spinning optics device of the invention as discussed above. As has been previously explained, each of the ophthalmic lens 10, 36 are arranged to be driven by a motor 53 (30) which is preferably a d.c. motor of a reversible type and which may be rotated either in a clockwise or counterclockwise direction at a selected range of speeds. In the preferred embodiment, the motor, such as motor 53 is provided with a velocity encoded 54 and in the embodiment of FIGS. 3 and 4, may be a gear motor as, in the treatment of a patient utilizing the spinning optics device of the invention, the lenses are driven at relatively low speeds.

The control system of the invention, which is connected to the motor 53 by means of conductors 60, includes memory means such as a memory 86 which may be a 256 by 4 bit RAM. The memory 86 is of the type in which digital data is stored and is provided with four output terminals identified as $b_0$, $b_1$, $b_2$ and $b_3$. In the illustrated embodiment, the memory 86 there provides a four bit output. However, it should be understood that two of such memories 86 should be used since each motor 53 43 requires four bits as explained hereinafter so that the total memory provides an eight bit output for the bits used to control a plurality of operating modes for each of the motors 53. New microprocessor technology will enable a larger memory capacity. The operating modes for the motors 53 include at least motor speed and direction of rotation.

The bits for each motor 53 are assigned as follows:

TABLE

| | | | |
|---|---|---|---|
| MOTOR DIRECTION: | $b_3$ $b_2$: | 00 Stop<br>01 Clockwise | 10 Counter clockwise<br>11 Reset counter |
| MOTOR SPEED: | $b_1$ $b_0$: | 00 Slow<br>01 Medium<br>11 Fast | |

In the above Table, $b_3$ is the most significant bit (MSB) and $b_0$ is the least significant bit (LSB). For example, the four bit byte 0100 is the code for the motor 53 to turn clockwise at a slow speed.

Means are provided for reading the digital data sequentially from the memory 86. More specifically, the control system of FIG. 13 includes an address counter 87 which, in the illustrated embodiment, is a fourteen bit counter and addresses the memory 86 with eight bits starting with bit 4 (bits 2 and 3 not being available). The counter 87 is incremented by a type 555 timer 91 having an output terminal 92 connected to the clock input terminal 88 of the counter 87. By means of a source of power, as shown in FIG. 14 and as will be described hereinafter, a +5 V is applied to the Vcc terminal 93 and to the reset terminal 94 of the clock or timer 91. The +5 V power supply is also connected through a potentiometer 96 to the threshold, discharge and trigger terminals 97–99 respectively and through a timing capacitor 101 to ground.

In one embodiment of the invention, the counter 87 is incremented by the type 555 clock 91 every 0.625 seconds which results in the fourth bit being incremented every five seconds. With a new operating mode for the motor 53 selected every five seconds, the entire memory contents of the memory 86 are cycled through once in twenty-one minutes and twenty seconds. It should be understood that this five second period has been arbitrarily selected as a starting place and may be increased or decreased as desired. To change this timing period, only the timing resistor 96 of the clock 91 need be changed.

If the counter 87 is to be reset ($b_3b_2=11$) it should be in the left side memory in order to conserve the logic required in the control circuit and to reduce the amount of power required. Otherwise, any binary code may be in either side.

Means are provided for feeding the digital data from the memory 86 to the motor 53 to operate the motor 4 in the plurality of operating modes which include variations in the speed of the motor 53 and the direction of rotation. More specifically, bits $b_0$,$b_1$ in the four bit byte outputed from the memory 86 and constituting a first portion of the digital data represent the selected speed of the motor 53. Bits $b_2$, $b_3$, which constitute a second portion of the digital data from the memory 86, represent the direction of rotation for the motor 53. Bits $b_0$,$b_1$ are conducted by conductors 101,102 to a digital/analog converter 103 having a non-inverting input 104, an inverting input 106 and an output 107. Conductor 101 is connected through resistor 108 to the inverting input 106 of operational amplifier 103. Conductor 102 is connected through resistors 109,111 to conductor 112 connected to the output 107 of the operational amplifier 103 and to the control input 113 of a pulse generator 114 through a potentiometer 116. Conductor 102 is also connected between resistors 109,111 to inverting input 106 of amplifier 103 by conductor 117. The non-inverting input 104 of amplifier 103 is connected to a voltage divider comprising resistors 118,119 and to the +5 V power supply.

The pulse generator 114 is also a type 555 timer or clock which produces negative going pluses at its output terminal 121, which are inverted into a train of positive pulses by inverter 122. As in the case of type 555 clock 91, clock or pulse generator 114 has its reset terminal 123 and its Vcc terminal 124 connected to the +5 V power supply which is also connected through potentiometer 126 to the threshold, discharge and trigger terminals 127, 128, 129 of the clock 114 and through a timing capacitor 131 to ground.

The circuit which includes the operational amplifier 103 is a simple operational amplifier inverting adder and, in the illustrated embodiment, the inputs are defined as a logic "1" having a value of +2.5 volts and a logic "0" having a value of −2.5 volts with respect to the +2.5 volts reference voltage. As indicated in the above table, if both bits $b_0$, $b_1$ are 0 (slow speed), the D/A converter output is its most positive value. If both bits $b_0$, $b_1$ are 1, a nearly zero value output results. If one bit is 0 and the other is 1, the output is the reference voltage +2.5 volts. As can be understood, the output from the D/A converter is fed to the control voltage terminal of the type 555 pulse generator 114 which changes the voltage to which the timing capacitor 131 is allowed to charge and therefore the time it takes. Therefore, the D/A voltage changes the clock output frequency and thereby the motor speed as will be explained hereinafter. It should be understood that the input of the D/A converter is a digital logic level and the output is an analog voltage.

The potentiometer 116 between the D/A converter 103 and the pulse generator 114 controls the amount that the pulse frequency is pulled from the nominal value. By adjusting the value of the potentiometer 116 and the other resistors associated with the operational amplifier 103, almost any speeds may be selected for the designations "slow", "medium", or "fast". The pulse train outputted from the pulse generator 114 by inverter 122 is fed to inputs 132, 133 of AND gates 134, 136. Also the AND gate inputs 137, 138 are connected by means of conductors 139, 141 to the terminals of the memory 86 from which bits $b_2$, $b_3$ are outputted. Thus, the bits $b_2$, $b_3$ representing the direction in which the motor 53 is driven, as indicated by the above table, are ANDed with the pulses from the clock 114 and the outputs 142, 143 of AND gates 134, 136 are fed to the non-inverting inputs 144, 146 of the power amplifiers 147, 148 respectively, the outputs 149, 151 of which are connected to opposite sides of the motor 53 through conductors 60.

The inverting inputs 152, 153 of amplifiers 146, 147 respectively are connected by means of conductor 154 to the junction 156 of the voltage divider represented by resistors 118, 119. It can be understood, if bits $b_3$, $b_2$ are 00, the outputs from the AND gates 134, 136 are both zero. If $b_2$,$b_3$ are 10, the positive going pulses appear at the output of one gate while the output of the other gate is zero. If $b_2$, $b_3$ equal 01, the reverse situation occurs.

Means are provided for resetting the counter 87. More specifically, the reset function is performed by and AND gate 155 having inputs connected by means of conductors 157, 158 to the conductors 141, 139 respectively so that bits $b_2$, $b_3$ are at the inputs to the gate 155. The output from gate 155 is connected through resistor 159 by means of conductor 161 to the reset terminal 89 on the counter 87 and through a reset pushbutton 162 to the +5 V power supply. The counter 87 will be reset when $b_3$, $b_2$ equal 11 or when the manual reset pushbutton 162 is pushed. This manual control provided by the pushbutton 162 permits the counter 87 to be reset when the control unit represented by the circuit of FIG. 13 is first started. Otherwise, the sequence will begin at some random position in the memory 86.

The amplifiers 147, 148 are operated at a higher voltage than the other portions of the circuit of FIG. 13 for greater amplitude pulses for driving the motor 53. In each of the amplifiers 147, 148, the inverting inputs 152, 153 are set at +2.5 volts by the voltage divider comprising resistors 118, 119. The non-inverting inputs 144, 146 are connected to the logic outputs 142, 143 of AND gates 134, 136 respectively. If an AND gate outputs a logic "0", the non-inverting input to the amplifier is 2.5 volts below the inverting input and the output is driven into negative saturation (0.8 v). If a logic "1" is output, the non-inverting input is 2.5 volts above the inverting input and the output is driven into positive saturation (11 volts with a 12 volt power supply). Thus the linear amplifiers 147, 148 act like a digital device with the output normally at ground and driven to the power supply voltage when the pulses are gated to it.

For each pulse from the amplifiers 147, 148 the motor 53 rotates an infinitesimal amount. For a series of pulses (nominal frequency of 3 kHz), the motor 53 rotates at a constant speed. The speed of the motor 53 is proportional to the average value of the pulse train from the clock 114 so that when the frequency is changed the speed is changed. In this manner, a precise speed control for the motor 53 is obtained. If both AND gates 134, 136 output a logic "0", both amplifier outputs are at 0.8 volts and the motor 53 will not turn. Similarly, if both gates 134, 136 output a logic "1" (reset) both power amplifier outputs are at 11 volts and again no rotation is produced as both sides of the motor 53 are at the same potential. It should be understood that the timing or duration of a particular operating mode for the motor 53 is determined by the program in the memory 86.

Referring now to FIG. 14, the power supply for the circuit of FIG. 13 may be battery operated and includes two batteries 161, 162 and three regulators 163, 164 and 166. Regulator 163, connected between the batteries 161, 162 provided a +5 V output voltage which remains on so as to maintain the digital data in the memory 86. Regulator 164 which provides an output power voltage of +12 volts is connected through a switch 167 to the batteries 161, 162 by means of conductor 168. Regulator 166 the output of which provides a +5 V for the logic voltage is connected to conductor 168 by conductor 169. It should be understood that although the power supply of FIG. 14 utilizes batteries, it is within the scope of the invention to provide power from an AC power supply which is rectified to provide the output DC voltages shown in FIG. 14 from the regulators 163, 164 and 166.

As shown in FIG. 15, a memory to tape interface and a tape to memory interface may be utilized in the control circuit of the invention as a means for logically transferring the program of instructions from an associated computer to the memory chip of the control circuit and as a means for logically transferring the data from the control circuit memory chip to the motor whose final performance will match exactly with the original computer programming instructions. Thus, the program which will be used in the control circuit of the invention is stored in a mass storage device (magnetic or paper computer tape, cassette tape, disc or any other computer peripheral) and then transferred into the control circuit memory by an interface. This interface is independent of the control circuit and the spinning optics device of the invention. Once the memory of the control circuit is loaded, the interface is no longer required for the operation of the control circuit of the invention.

As shown in the memory to tape interface portion of the diagram of FIG. 15, front panel controls 170 are connected to logic circuitry 171 having a clock output 172 connected to the input of an address counter 173. The address counter 173 addresses memory 174 and output data is fed to a shift register 17 connected to outputs 177, 178 of the logic circuitry 171. The output 179 of the shift register 176 is fed to a type 555 tone oscillator 181 having an output 182 connected to the input 183 of an audio amplifier/adder/filter 184. A second type of 555 tone oscillator 186 connected logic circuitry 171 through ports 187, 188 respectively has an port 189 connected to the input 199 of the audio amplifier 184. A type 555 clock 192 is also connected between ports 187, 188. The audio amplifier output port 193 provides an audio output as shown.

In the tape to memory interface also is shown in the lower part of FIG. 15 audio is introduced to input 194 of an audio amplifier/limiter 196 having an output 197 connected to the inputs 201, 202, 203, 204 of tone detectors 206, 207, 208, 209 respectively. Outputs 211, 212 of detectors 206, 207 respectively are connected to logic circuitry 213 and output 216, 217 of detectors 208, 209 respectively are connected to logic 218. Logic circuits 213, 218 are interconnected at 219 and to an error/reset signal source 221. The output of logic circuit 213 is connected to shift register 222 and the output of logic circuit of 218 is connected to a clock 223.

| Write Sequence | | |
|---|---|---|
| 1. Load Shift Reg | "write" } | 9 shift $b_6$ |
| 2. Inc Mem Counter | "0" } | 10 shift $b_7$ |
| 3. Shift $b_0$ (sync) | | 11 shift $b_8$ |
| 4. Shift $b_1$ (sync) | | 12 shift $b_9$ |
| 5. Shift $b_2$ | | 13 shift $b_{10}$ |
| 6. Shift $b_3$ | | 14 shift $b_{11}$ |
| 7. Shift $b_4$ | | 15"write""0" |
| 8. Shift $b_5$ | | 16"write""0" |

To avoid sync problems with serial date due to incorrect tape speed the tape will carry a second tone which will serve as the clock during the read mode.

The tones go on tape as binary frequency shift keying (FSK) with the nominal tone (A) indicating "0" and the shifted tone (B) indicating "1".

The maximum bit rate will be determined by the tape frequency response. Expensive tape should not be used since cheap cassette recorders are limited to about 15 KHZ. At a bit rate of 3000 BPS an entire program can be read from tape-or transferred to the control memory in about 1 second.

Address and Data displays can be 3 digit octal or 2 digit Hex. Data is input from the front panel by thumbwheel switches.

No input for computer generated paper tape is anticipated.

CONTROLLER/TAPE INTERFACE

Required Modes:

| | |
|---|---|
| 1. Read from tape<br>2. Write to tape | Tone decoders & generators |
| 3. Read Manual Input<br>4. Display Memory Contents | Internal Memory to/from front panel |
| 5. Load Control Memory<br>6. Damp Control Memory | Internal Memory to/from spinning optics memory |

A 12 bit shift register converts serial to parallel and parallel to serial data

Bits 1-08 control data

Bits 9-10 interface command

Bits 11-12 Sync-always "1"

A 4 bit binary counter counts 16 states for Tape Read/-Write Sequencing:

| Read Sequence | | | |
|---|---|---|---|
| 1. Shift (sync) | $b_0$ | 9. Shift | $b_8$ |
| 2. Shift (sync) | $b_1$ | 10. Shift | $b_9$ |
| 3. Shift | $b_2$ | 11. Shift | $b_{10}$ |
| 4. Shift | $b_3$ | 12. Shift | $b_{11}$ |
| 5. Shift | $b_3$ | 13. | Load Mem |
| 6. Shift | $b_5$ | 14. | Increment counter |
| 7. Shift | $b_6$ | 15. nothing | |
| 8. Shift | $b_7$ | 16. nothing | |

OP CODES

00 Load memory & increment counter

01 Load program number & reset counter

10 Halt Reading/disable input/signal ready

11 Nothing

There can be many programs on a tape. The first data word is the program number. The number desired is set by thumbwheel switches. When it matches the number from tape the program is reading otherwise it is not. After the selected program is reading the reading operation terminates and a "Ready" signal is lit.

What is claimed is:

1. A control circuit for rotating an ophthalmic lens rotatably mounted on a frame comprising, in combination: a source of electric power; a variable speed, reversible D.C. electric motor driveably connected to said lens; a memory having a digital data stored therein representing a plurality of operating modes for said motor; means for reading said digital data sequentially from said memory; and means for feeding said digital data from said memory to said motor to operate said motor in said plurality of operating modes; wherein said operating modes for said motor include a plurality of motor speeds, direction of rotation and duration of operation of said motor; wherein said means for reading data sequentially from said memory include an address counter having an output connected to said memory, means for resetting said address counter and a clock connected to said source of power for incrementing said address counter; and wherein said means for feeding data from said memory to said motor include a pulse generator having a control input and an output for providing a pulse train, means for conducting said pulse train from the output of said pulse generator to said motor to drive said motor, means for conducting a first portion of the digital data from said memory to said pulse generator to vary the frequency of said pulse train thereby varying the speed of said motor.

2. A control circuit in accordance with claim 1 wherein said means for feeding the data from said memory to said motor further include gating means for applying a second portion of the digital data from said memory to said motor for rotation of said motor selectively in either direction.

3. A control circuit in accordance with claim 2 wherein said means for conducting the first portion of the data from said memory to said pulse generator include a digital/analog converter having an input connected to said memory and an output connected to the control input of said pulse generator.

4. A control circuit in accordance with claim 3 wherein said gating means include a pair of AND gates each having an output and a pair of inputs, means for connecting the outputs of said AND gates to the opposite side of said motor, means for conducting said second portion of the digital data from said memory to one of the inputs of each of said AND gates and wherein said means for conducting said pulse train from said pulse generator include means for connecting said pulse generator output to the other input of each of said AND gates.

5. A control circuit in accordance with claim 4 wherein said means for connecting each of the outputs of said AND gates to opposite sides of said motor include a pair of power amplifiers, each of said power amplifiers being connected between one of said outputs of said AND gates and one side of said motor.

6. A control circuit in accordance with claim 5 wherein said address counter is provided with a reset terminal and means for conducting said second portion of said digital data from said memory to said counter reset terminal.

7. A control circuit in accordance with claim 6 further including switch means for connecting said counter reset terminal to said source of power.

8. A control circuit in accordance with claim 7 wherein said means for conducting said second portion of said digital from said memory to said counter reset terminal include an AND gate having an output connected to said counter reset terminal and a pair of inputs connected to said memory for conducting said second portion of said digital data to said AND gate.

9. A control circuit for rotating an ophthalmic lens rotatably mounted on a frame, the circuit comprising, in combination: a source of electric power, a variable speed, reversible electric motor driveably connected to said lens, a memory having digital data stored therein representing a plurality of operating modes for said motor, means for reading said digital data sequentially from said memory and means for feeding said digital data from said memory to said motor to operate said motor in said plurality of operating modes, and wherein said means for feeding data from said memory to said motor include a pulse generator having a control input and an output for providing a pulse train and means for conducting at least a portion of said pulse train from the output of said pulse generator to said motor to drive said motor and vary its operating mode.

10. A control circuit in accordance with claim 9, wherein said operating modes for said motor include a plurality of motor speeds, direction of rotation, and duration of operation of said motor.

11. A control circuit in accordance with claim 10, wherein said means for reading data sequentially from said memory include an address counter having an output connected to said memory, means for resetting said address counter and a clock connected to said source of power for incrementing said address counter.

12. A control circuit in accordance with claim 9, wherein said motor comprises a DC motor.

* * * * *